(12) United States Patent
Tatum et al.

(10) Patent No.: US 6,808,441 B2
(45) Date of Patent: Oct. 26, 2004

(54) DENTAL TOOL SHARPENER AND METHOD OF USE

(75) Inventors: Robert W. Tatum, Bartlett, IL (US); Timothy S. Irwin, Oswego, IL (US)

(73) Assignee: Nordent Manufacturing, Inc., Elk Grove Village, IL (US)

(*) Notice: Subject to any disclaimer, the term of this patent is extended or adjusted under 35 U.S.C. 154(b) by 42 days.

(21) Appl. No.: 10/359,903

(22) Filed: Feb. 7, 2003

(65) Prior Publication Data

US 2004/0157537 A1 Aug. 12, 2004

(51) Int. Cl.⁷ .................................................. B24B 1/00
(52) U.S. Cl. ........................... 451/48; 451/28; 451/45; 451/177; 451/187; 451/224
(58) Field of Search .............................. 451/28, 45, 48, 451/177, 187, 224

(56) References Cited

U.S. PATENT DOCUMENTS

| | | |
|---|---|---|
| 506,613 A | 10/1893 | Wilbur |
| 679,027 A | 7/1901 | Knowlton |
| 705,226 A | 7/1902 | Ettinger |
| 921,986 A | 5/1909 | Hanson |
| 945,137 A | 1/1910 | Olds |
| 1,110,366 A | 9/1914 | Wincrantz |
| 1,138,355 A | 5/1915 | Carr |
| 1,230,111 A | 6/1917 | Callaway |
| 1,308,088 A | 7/1919 | Loomer |
| 1,350,951 A | 8/1920 | Artmaier |
| 1,605,320 A | 11/1926 | Bates |
| 2,114,757 A | 4/1938 | Yerkes |
| 2,275,496 A | 3/1942 | Berg |
| 2,366,671 A | 1/1945 | Montelius |
| 2,380,988 A | 8/1945 | Mudler |
| 2,415,121 A | 2/1947 | Wiken et al. |
| 2,435,671 A | 2/1948 | Clark et al. |
| 2,596,916 A | 5/1952 | Raney |
| 2,911,771 A | 11/1959 | Amiet |
| 3,894,358 A | 7/1975 | Lorenz |
| 4,106,242 A | 8/1978 | McCandless et al. |
| 4,528,778 A | 7/1985 | Wolff |
| 4,535,570 A | 8/1985 | Ochiai et al. |
| 5,030,091 A | 7/1991 | Svanberg |
| 5,157,870 A | 10/1992 | Pike |
| 5,197,227 A | 3/1993 | Svanberg |
| 5,582,542 A | 12/1996 | Stein |
| 5,645,468 A | 7/1997 | Svanberg |
| 5,667,427 A * | 9/1997 | Airhart et al. ................ 451/45 |
| 5,934,975 A | 8/1999 | Svanberg |
| 6,142,856 A | 11/2000 | Römhild |
| 6,149,431 A | 11/2000 | Svanberg |
| 6,254,464 B1 * | 7/2001 | Kawata ..................... 451/164 |
| 6,393,712 B1 | 5/2002 | Jansson |

* cited by examiner

*Primary Examiner*—Joseph J. Hail, III
*Assistant Examiner*—Shanlese McDonald
(74) *Attorney, Agent, or Firm*—Brinks Hofer Gilson & Lione

(57) ABSTRACT

A dental tool sharpener is disclosed having a base. A grinding surface is rotatably attached to the base about a fixed axis, the axis of rotation being perpendicular to the base. a positioner is attached to the base and aligns a top face of a blade of a dental tool such that the top face is substantially perpendicular to the axis of rotation of the grinding surface. A gripper is attached to the base for grasping the dental tool and for transporting the dental tool from the positioner to the grinding surface while maintaining the top face substantially perpendicular to the axis of rotation of the grinding surface.

27 Claims, 8 Drawing Sheets

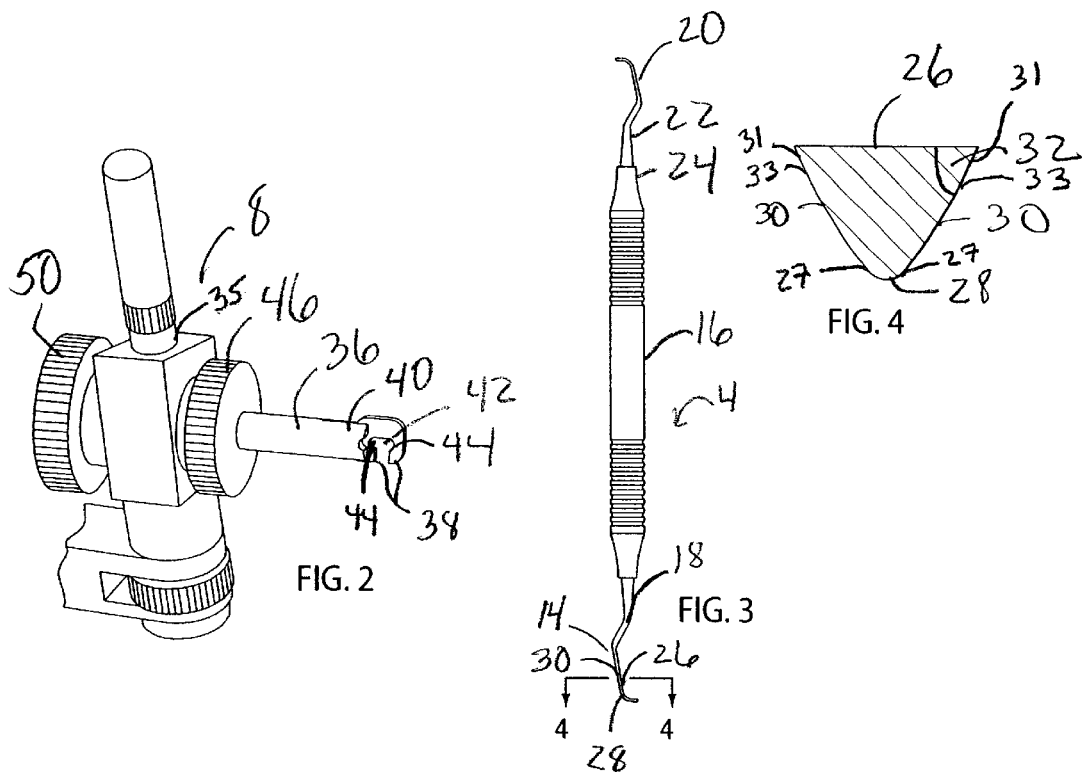

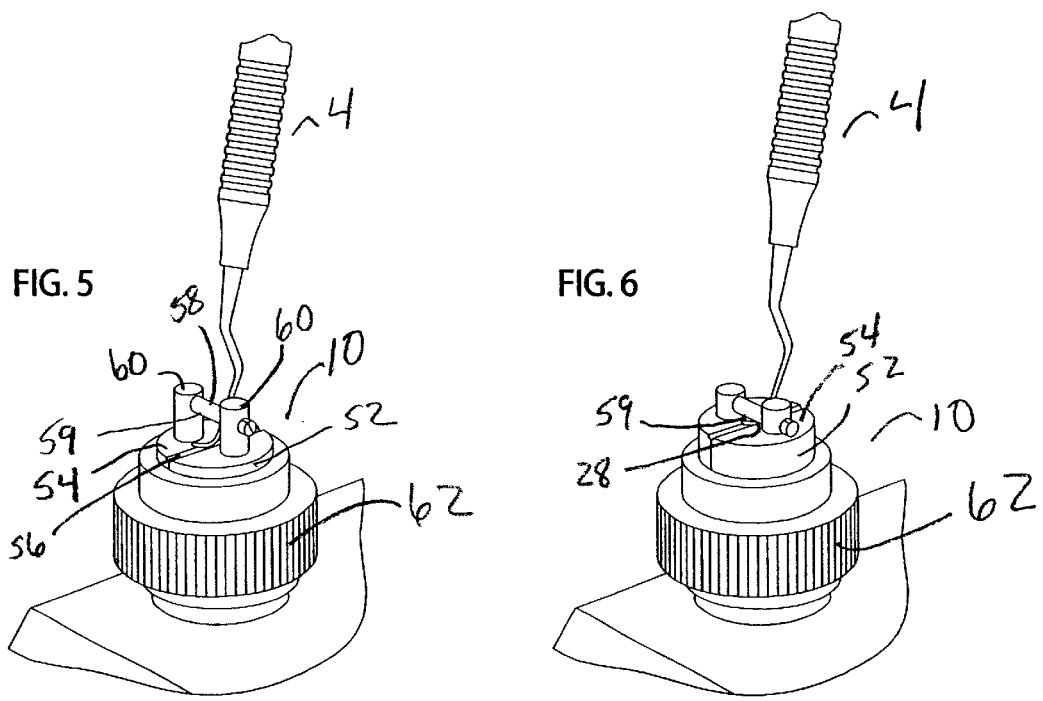

DENTAL TOOL SHARPENER AND METHOD OF USE

BACKGROUND

The present invention relates to blade sharpening equipment and, more specifically, to a machine for sharpening the blades of dental tools.

The scaling and root planing of teeth for the removal of calculus (commonly known as plaque) is important for the treatment and prevention of periodontal diseases. For this purpose, dental tools such as curets or scalers are employed for the scaling of the root surfaces of teeth. This allows thin chips of calculus to be removed from the root surfaces of the teeth, where plaque will most often gather. When scaling the root surface of teeth, it is essential that the edge of the blade of the dental tool have a predetermined angle.

The scaling and root planing procedures will often dull the edge of the blade of the dental tool. Thus, the edges of the blade often need to be sharpened so that the proper angle is maintained. A variety sharpening techniques and machines are employed. For example, blades will often be sharpened "free-hand." This will entail a user holding the handle of a tool and bringing it into contact with a hand-activated sharpening stone by moving the stone back and forth over the blade of the dental tool. This may result in the unfortunate consequence of improperly sharpened blade edges having the incorrect angle.

Another technique is to employ a sharpening machine. The machine will often have a type of guide or plate for holding the dental tool. The machine will also include a sharpener, and the sharpener and the tool will be brought into contact with each other so that the blade of the tool may be sharpened. These types of machines, however, are often designed to work with a specific manufacturer's version of curets or scalers. Moreover, because these machines involve the movement of both the guide and the sharpener, there are a large number of animated parts, thus increasing complexity of use and the chance of user error or machine malfunction.

BRIEF SUMMARY

A dental tool sharpener for the sharpening of blades of dental tools is presented herein. The dental tool sharpener includes a base and a grinding surface rotatably attached to the base about a fixed axis. The axis of rotation is perpendicular to the base. A positioner is attached to the base for aligning a top face of a blade of a dental tool such that the top face is substantially perpendicular to the axis of rotation of the grinding surface. A gripper is attached to the base for grasping the dental tool and for transporting the dental tool from the positioner to the grinding surface while maintaining the top face substantially perpendicular to the axis of rotation of the grinding surface.

Another aspect of the dental tool sharpener includes a base and a grinding surface rotatably attached to the base about an axis fixed at a predetermined angle relative to a plane parallel to the base. The grinding surface includes a contact surface for contacting a blade of a dental tool. A gripper is attached to the base for grasping the dental tool. A positioner is attached to the base and aligns a top face of the blade of the dental tool such that a contact angle of the blade and a contact angle of the contact surface are complementary. The contact angle of the blade is defined by a top face and a side face of the blade and the contact angle of the contact surface is defined by the contact surface and a plane parallel to the top face of the blade as aligned by the positioner.

The invention also includes a method for sharpening a blade of a dental tool with a dental tool sharpener. The dental tool sharpener includes a base and a positioner, a gripper and a grinding surface each attached to the base. The method includes aligning a top face of the blade in the positioner such that the top face is set at a fixed angle relative to the grinding surface such that a contact angle of the blade is complementary to a contact angle of the grinding surface. The contact angle of the blade is defined by a top face and a side face of the blade and the contact angle of the contact surface is defined by the contact surface and a plane parallel to the top face of the blade as aligned by the positioner. The shank is then grasped with the gripper and the dental tool is moved with the gripper from the positioner to the grinding surface. A first side face of the blade is contacted with a contact surface of the grinding surface is passed over the contact surface.

The dental tool sharpener described herein helps to ensure that the blade of a dental tool will be properly aligned before contacting the sharpening element, without requiring precise positioning. Once the blade has been aligned by the positioner, manipulation of the dental tool to align the blade with the grinding surface is not required. The foregoing and other features and advantages will become further apparent from the following detailed description of the presently preferred embodiments, read in conjunction with the accompanying drawings.

BRIEF DESCRIPTION OF THE DRAWINGS

FIG. 2 is a sectional view of a gripper associated with the dental tool sharpener of FIG. 1;

FIG. 3 is a view of a dental tool;

FIG. 4 is a cross-sectional view of the dental tool of FIG. 3 taken along the line 4—4;

FIG. 5 is a sectional view showing a positioner associated with the dental tool sharpener of FIG. 1 in a lowered position and a dental tool;

FIG. 6 is a view of the positioner and dental tool of FIG. 5 showing the positioner in a raised position;

DETAILED DESCRIPTION OF THE DRAWINGS AND THE PRESENTLY PREFERRED EMBODIMENTS

Figure 1:
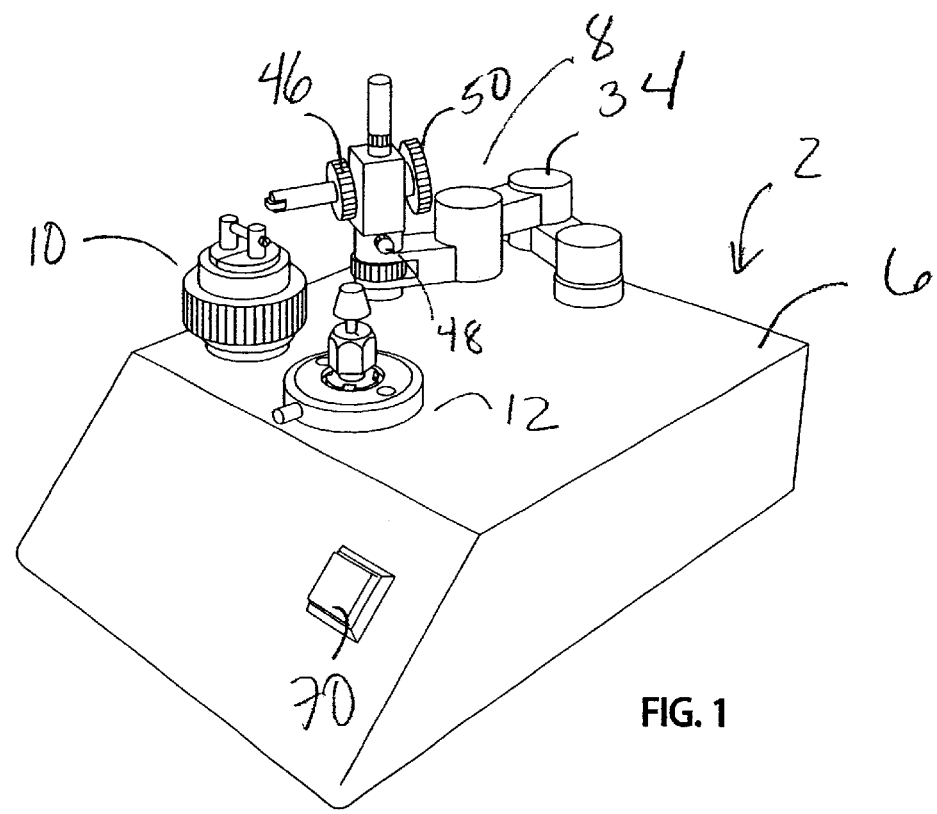
FIG. 1 is a perspective view of a dental tool sharpener.

Referring to FIG. 1, a dental tool sharpener 2 for sharpening a dental tool 4 (FIG. 3) is now described herein. The dental tool 4 includes a blade 14, a handle 16 and a shank 18 that connects the blade to the handle. Optionally, and as shown in FIG. 3, the dental tool may include an additional blade 20 and shank 22 at an end 24 of the handle 16 opposite the blade 14 and shank 18. As is known in the art, the dental tool 4 herein described is used for the cleaning and scaling of teeth. The teeth are cleaned by scaling the root surfaces of the teeth with the blade of the dental tool, which will result in any plaque build-up that may be present being removed. As described in more detail below, any of a number of types or patterns of dental curets and scalers may be sharpened with the sharpener 2.

The blade 14 of the dental tool 4 includes a top face 26 and a pair of opposing side faces 30. As shown in FIG. 4, each side face 30 is set at an angle with respect to the top face 26. This angle is known as a contact angle and is denoted as 32. The contact angle 32 provides a scaling edge 33 that scales the root surfaces of teeth. The contact angle 32 is preferably in the range of 72 through 76 degrees inclusive, and most preferably is 75 degrees. Of course, the contact angle may also have other values depending on industry and specification requirements. It is desirable that a substantially constant contact angle be maintained so that the dental tool remains effective. So that the contact angle 32 is maintained, the side faces 30 must frequently be sharpened.

The blade also includes a bottom edge 28 that is formed by an end 27 of each side face 30 opposite an end 31 where the side face 30 meets the top face 26. The bottom edge 28 may be either semi-circular or triangular in cross-section.

Figure 8:
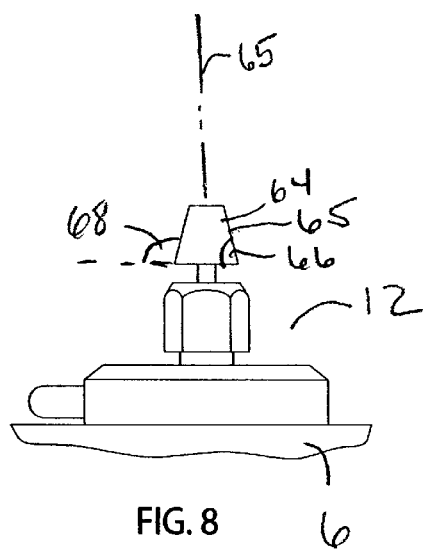
FIG. 8 is a sectional view of a sharpening element associated with the dental tool sharpener of FIG. 1.

The sharpener 2 includes a base 6, a gripper 8, a positioner 10, and a sharpening element 12 each attached to the base 6. Referring to FIG. 8, the sharpening element 12 includes a grinding surface 64 that is rotatably attached to the base 6. The grinding surface 64 rotates about a fixed axis that is perpendicular to the base 6. The axis of rotation of the grinding surface 64 is denoted as 65 in FIG. 8. The grinding surface 64 may, by way of example, be a grinding surface made from diamond-coated steel, although in other embodiments, materials such as a mounted abrasive stone or ceramics may be used.

In a preferred embodiment, the grinding surface 64 is conically-shaped, and the manufacturing angle of the grinding surface, denoted as 66, is approximately equal to the contact angle of the blade 14 of the dental tool 4. Thus a contact angle of the grinding surface 64, which is complementary to the manufacturing angle 66 of the grinding surface 64 and is denoted as 68, is approximately complimentary to the contact angle 32 of the blade 14. Note that the contact angle 68 is the angle of a surface 65 of the grinding surface that contacts the blade 14 relative to a plane perpendicular to the axis of rotation of the grindstone.

The sharpening element 12 is actuated through the use of a switch 70. Although a preferred embodiment utilizes a motor and power cord that attaches to an electrical outlet to power the sharpening element, other methods may also be used, such as, by way of example, through the use of a battery, pneumatics or hydraulics.

Referring to FIG. 2, the gripper 8 includes an articulated arm 34 that is moveable in a plane substantially perpendicular with the axis of rotation 65 of the grinding surface 64. As will be described more fully below, the arm 34 facilitates the movement of the dental tool 4 between the positioner 10 and the sharpening element 12. Although a preferred embodiment includes a three-jointed, or segmented, arm, in other embodiments the arm may have a different number of joints so long as the arm is able to transport the dental tool between the positioner and the sharpening element.

The gripper 8 includes a chuck 36 that has a pair of jaws 38 located at an end 40 of the chuck 36. As will be described more fully below, the jaws 38 grasp the shank 22 of the dental tool 4. Preferably, and as shown in FIG. 2, the jaws 38 include a recess 42 that has opposing rounded edges 44. When the jaws 38 grasp the shank 22 of the dental tool 4, the shank 22 is contained within the recess 42.

Preferably, the gripper 8 also includes numerous adjustment dials for the adjustment of the chuck 36 and jaws 38. Although a preferred embodiment contemplates the use of dials, other adjustment devices may be used, such as, by way of example, levers, pushbuttons, or any combination therein. A dial 50 is included so that the jaws may be adjusted from a fully closed position (i.e., jaws in contact with each other) to a fully open position, as well as various positions in between. A detent dial 46 is provided so that when the detent dial 46 is rotated, the chuck 36 and jaws 38 together rotate about an axis parallel to the base 6 so that the jaws 38 may be set at various positions. A height adjustment dial 48 is also included and allows the height of the chuck and jaws to be adjusted along a shaft 33 extending perpendicularly from the articulated arm 34.

Referring to FIG. 5, the positioner 10 includes a platform 52 having a top surface 54 that is substantially perpendicular with the axis of rotation 65 of the grinding surface 64. The top surface 54 includes a groove 56 that preferably runs across the entire top surface 54, although in other embodiments the groove 56 may run a distance less than the entire top surface 54. The groove 56 acts as a guide for the positioning of the blade 14 of the dental tool 4 on the top surface 54. Preferably, the width of the groove 56 is approximately the same as or slightly larger than the width of the bottom edge 28. However, since the bottom edge 28 need not rest within the groove 56, in other embodiments the width of the groove 56 may be less than the width of the bottom edge 28 so that the bottom edge rests upon the groove.

The positioner 10 also includes a bar 58 that is positioned above the top surface 54. A pair of posts 60 attach the bar 58 to the top surface 54, although in other embodiments a single post may be used. A rotatable knob 62 associated with the positioner 10 allows the bar 58 to be vertically adjusted with respect to the top surface 54. This may be accomplished using mated threads on one or both posts and the knob. Any of a number of other mechanisms, such as hydraulics, pneumatics, an electric motor, or the like, may be used in other embodiments.

An alignment surface 59 on the bar 58 secures the blade 14 of the dental tool 4 to the top surface 54. The alignment surface 59 may be a continuous flat surface, or, in the alternative, may be several discrete flat surfaces. The alignment surface 59 is substantially perpendicular with the axis of rotation 65 of the grinding surface 64.

Thus, a dental tool and a dental tool sharpener have been described herein. Except as otherwise noted above, the parts that come into contact with the blade are made of stainless steel (except the grinding surface). Other suitable materials include, but are not limited to, hard plastics, ceramics, and other metals or a combination therein.

The method for sharpening a dental tool using the dental tool sharpener 2 described herein will now be provided. Referring to FIG. 5, the bottom edge 28 of the blade 14 of the dental tool 4 is placed upon the groove 56 of the top surface of the positioner 10. Note that the bar 58 should be raised with respect to the top surface 54 so that the bottom edge 28 may be placed upon the groove 56. The rotatable knob 62 is then manipulated so that the bar 58 is lowered and the alignment surface 59 comes into contact with the top face 26 of the blade 14. The bar 58 should continue to be lowered until the rotatable knob 62 can no longer be rotated, i.e., until the bar 58 cannot be lowered any further. FIG. 6 shows the blade of a dental tool secured by the bar 58 to the top surface 54.

Figure 7:
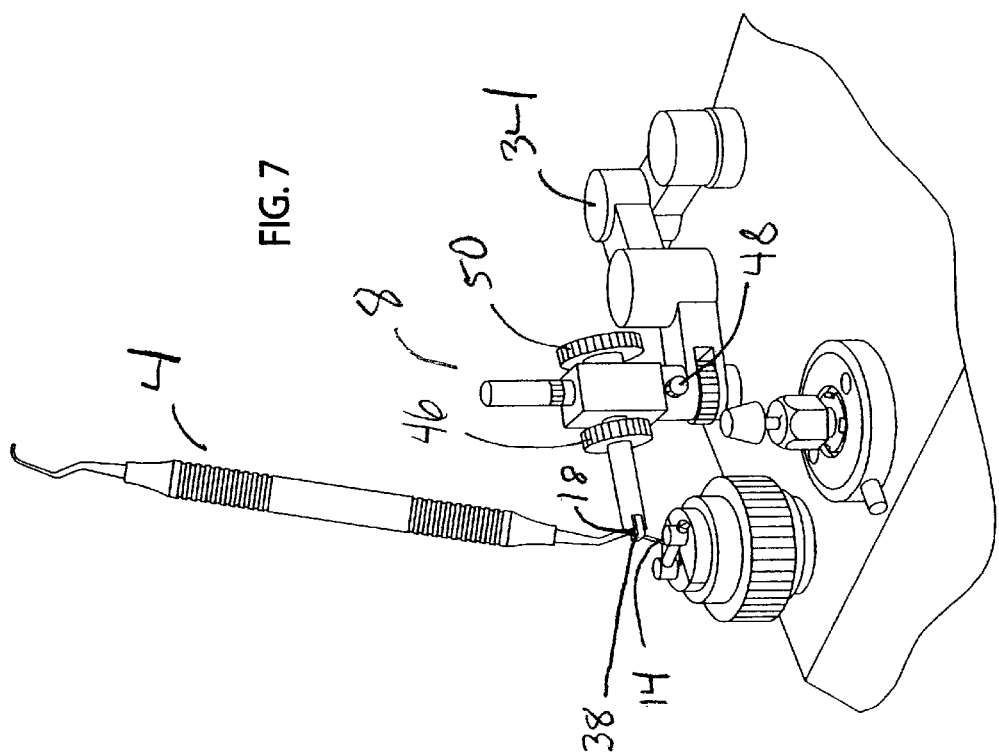
FIG. 7 is a view of the dental tool sharpener of FIG. 1 showing a dental tool being grasped by the gripper.

When the bar 58 can no longer be lowered, the top face 26 of the blade 14 will be substantially parallel to the alignment surface 59 of the positioner 10. The arm 34 of the gripper 8 is then moved towards the dental tool. The dial 50 may need to be rotated so that the jaws 38 are in an open position. The detent dial 46 and the height adjustment dial 48 may also be manipulated so that the jaws are aligned with the shank 22 of the blade 14. The jaws 38 are then moved forward so that the shank 22 enters the recess 42 of the jaws 38. The 50 dial can then be used to move the jaws 38 to a closed position and secure the shank 22 (FIG. 7).

Figure 9:
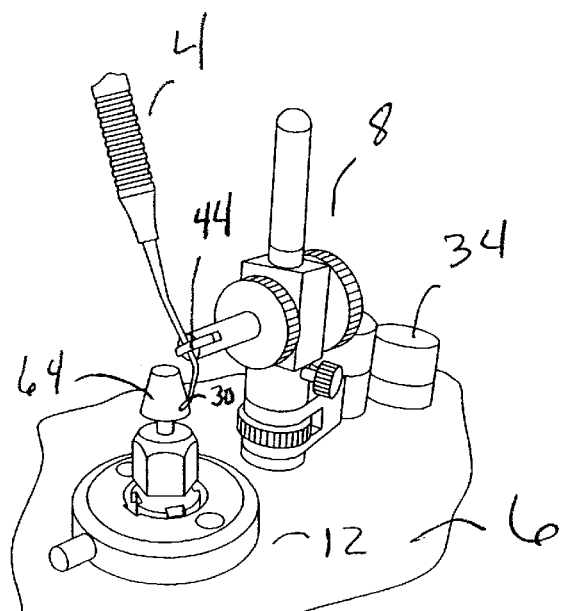
FIG. 9 is a sectional view showing a blade of the dental tool being sharpened by the sharpening element of FIG. 8.

The bar 58 is then raised so that the blade 14 is no longer secured to the positioner. The sharpening element 12 is then actuated and the arm 34 is manipulated to move the dental tool 4 towards the grinding surface 64 until the side face 30 comes into contact with the grinding surface 64. As shown in FIG. 9, each side face 30 of the blade 14 is then passed across the grinding surface 64 so that it is sharpened. The side face 30 should only need to be passed across the grinding surface once, although, of course, the side face may be passed over the grinding surface more than once.

Figure 10:
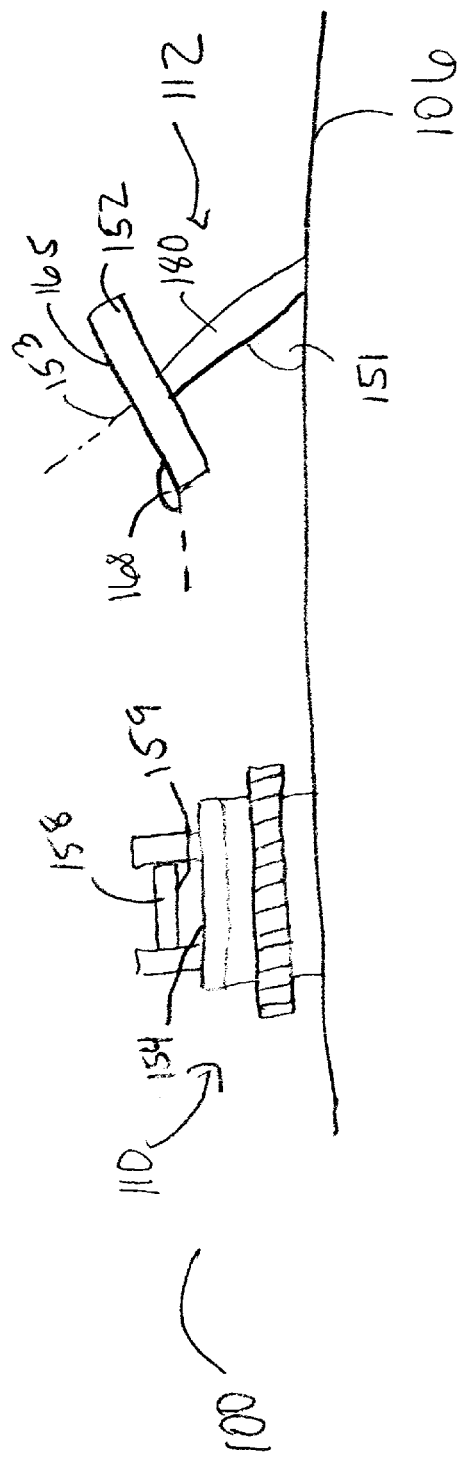
FIG. 10 shows a partial view of a first alternate embodiment of the dental tool sharpener.

FIG. 10 shows a partial view of an alternate embodiment of a dental tool sharpener 100. The dental tool used with the dental tool sharpener 100 is the same as the dental tool 4 described above, and for purposes of clarity has been omitted from the figure. A sharpening element 112 is rotatably attached to the base 106. The sharpening element includes a shaft 180 with a grinding surface 152 attached to it. The grinding surface 152 may be a disc or cylindrically shaped. The grinding surface 152 rotates about a fixed axis, denoted as 153, that is set at a predetermined angle 151 relative to a plane parallel to the base 106. The grinding surface 152 includes a contact surface 165 that may be either substantially parallel or substantially perpendicular to the axis of rotation 153, depending on the orientation of the grinding surface. The contact surface 165 and a plane parallel to the base 106 together define a contact angle that is denoted as 168. As described above, the contact angle of the grinding surface and the contact angle of the blade of the dental tool are complementary.

A positioner 110 is also included and is similar to the positioner described above. The positioner 110 includes a top surface 154 and a bar 158 having an alignment surface 159. The top surface 154 and the alignment surface 159 are substantially parallel to a plane that is parallel to the base 106. The method for aligning the top face of the blade and for the sharpening of the blade are the same as that described above, except that after one side face of the blade is passed over the grinding surface, the blade may have to be realigned with the positioner so that the other side face may be passed over the grinding surface so that the blade is properly sharpened.

Figure 11:
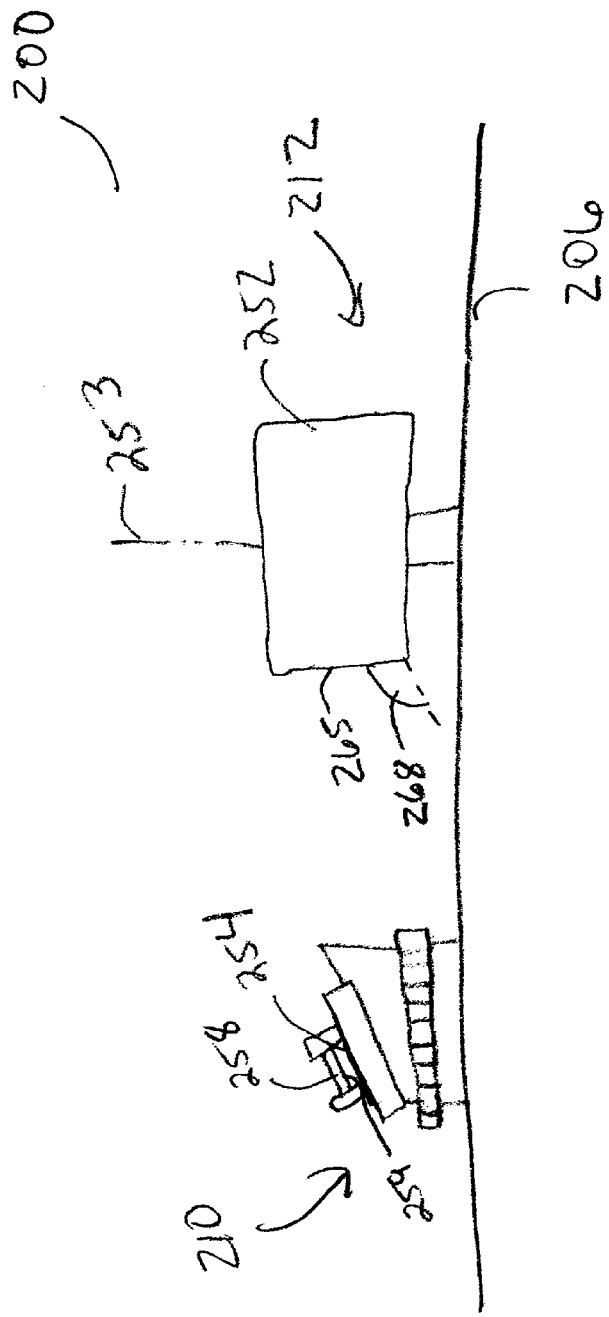
FIG. 11 shows a partial view of a second alternate embodiment of the dental tool sharpener.

FIG. 11 shows a partial view of another alternate embodiment of a dental tool sharpener 200. The dental tool used with the dental tool sharpener 200 is the same as the dental tool 4 described above, and for purposes of clarity has been omitted from the figure. A sharpening element 212 is rotatably attached to the base 206. The sharpening element includes a grinding surface 252 attached to it. The grinding surface 252 is disc or cylindrically shaped. The grinding surface 252 rotates about a fixed axis, denoted as 253, that is perpendicular to a plane parallel to the base 206. The grinding surface 252 includes a contact surface 265 that is substantially parallel to the axis of rotation 253.

A positioner 210 includes a top surface 254 and a bar 258 having an alignment surface 259. The top surface 254 and the alignment surface 259 are positioned so that when the top face of the blade is aligned by the positioner, using the same technique described above, the contact angle of the blade, defined as the angle formed by the top and side face, will be complementary to a contact angle, denoted as 268, of the grinding surface. The contact angle of the grinding surface is defined as the angle formed by the contact surface of the grinding surface and a plane parallel to the alignment surface of the positioner. The method to sharpen the blade is the same as that described above, except that after one side face of the blade is passed over the grinding surface, the blade may have to be realigned with the positioner so that the other side face may be passed over the grinding surface so that the blade is properly sharpened.

Figure 12:
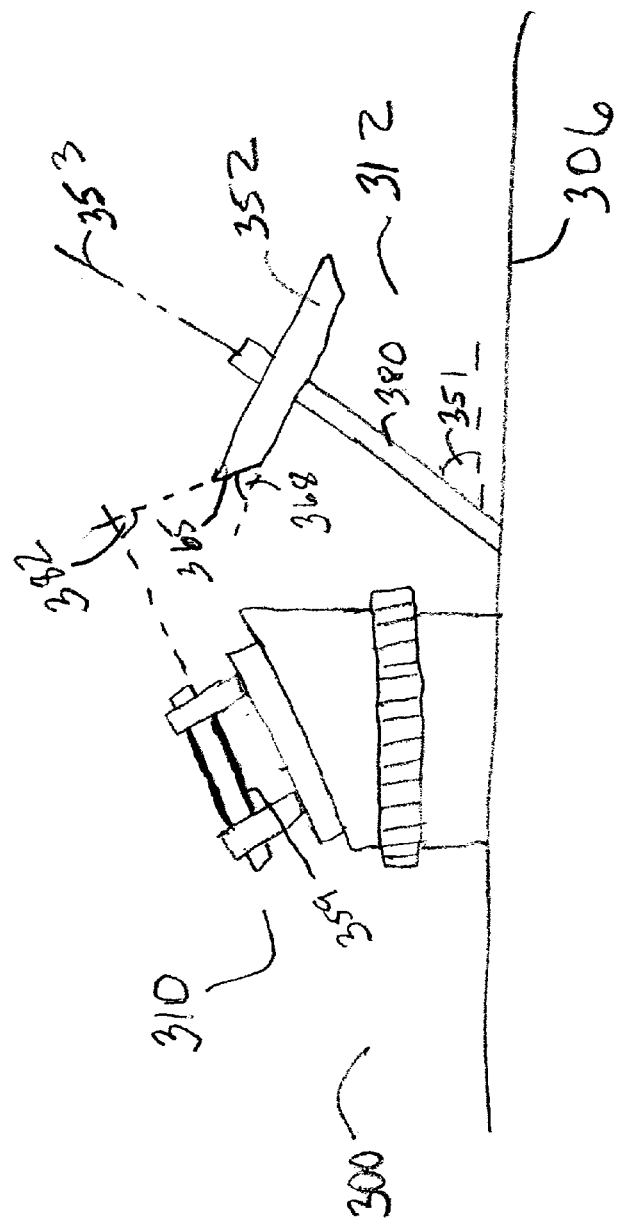
FIG. 12 shows a partial view of a third alternate embodiment of the dental tool sharpener.

FIG. 12 shows a partial view of another alternate embodiment of a dental tool sharpener 300, with only the differences being described. Note that the dental tool used with the dental tool sharpener 300 is the same as the dental tool 4 described above, and for purposes of clarity has been omitted from the figure. A sharpening element 312 is rotatably attached to a base 306. As one exemplary embodiment, the sharpening element includes a shaft 380 with a grinding surface 352 attached to it. The grinding surface 352 rotates about a fixed axis, denoted as 353, that is set at a predetermined angle 351 relative to a plane parallel to the base 306. The grinding surface 352 includes a contact surface 365 having a contact angle 368 defined by the contact surface 365 and a plane perpendicular to the axis of rotation 353.

The dental tool sharpener 300 also includes a positioner 310 having a top surface 354 and a bar 358 with an alignment surface 359. The top surface 354 and the alignment surface 359 are similar to the top surface and alignment surface described above. The top surface 354 and alignment surface 359 are oriented so that the alignment surface 359 and the contact surface 365 of the grinding surface 352 form a fixed angle, denoted as 382, such that the contact angle 368 of the grinding surface 352 will be complementary to the contact angle of the blade once the top face is aligned with the alignment surface 359. As noted above, the contact angle of the blade is formed by the top face and the side face of the blade.

Operation of the dental tool sharpener is similar to that described above. The blade is placed onto the top surface 354 of the positioner 310. The alignment surface 159 is then lowered towards the top surface 354 so that the top face of the blade comes into contact with the alignment surface 359. The top face of the blade will thus be positioned so that it is substantially parallel with the alignment surface 359. As noted above, the contact angle of the blade and the contact angle 368 of the grinding surface 352 are complementary. Thus, when the side faces are sharpened, the blade will maintain proper contact angles. However, and as noted with the embodiments described in FIGS. 10 and 11 above, after one side face of the blade is passed over the grinding surface the blade may have to be realigned with the positioner so that the other side face may be passed over the grinding surface so that the blade is properly sharpened.

Other alternate embodiments of the dental tool sharpener may also be utilized. For example, the articulated arm need not be moveable in a plane substantially perpendicular with the axis of rotation of the grinding surface. The arm may be otherwise movable so long as the position of the blade, after having been aligned by the positioner, is maintained.

The benefits of the above-described dental tool sharpener and method of use are numerous. Because, for example, the contact angle of the grinding surface is substantially complementary to the contact angle of the blade, the blade of the dental tool will be sharpened so that its contact angle is maintained. Other types of dental tool sharpeners often may require careful manipulation of the dental tool and a sharpening element to ensure that the dental tool blade is not improperly sharpened, thus rendering the blade ineffectual or unusable. The positioner of the dental tool sharpener described herein helps to ensure that the blade will be properly aligned before contacting the sharpening element, without requiring precise positioning. Once the blade has been aligned by the dental tool, manipulation of the dental tool to align the blade with the grinding surface is not required. It is therefore intended that the foregoing detailed description be regarded as illustrative rather than limiting, and that it be understood that it is the following claims, including all equivalents, that are intended to define the spirit and scope of this invention.

What is claimed is:

1. A dental tool sharpener, comprising:
   a base;
   a grinding surface rotatably attached to the base about a fixed axis, the axis of rotation being perpendicular to the base;
   a positioner attached to the base for aligning a top face of a blade of a dental tool such that the top face is substantially perpendicular to the axis of rotation of the grinding surface; and
   a gripper attached to the base for grasping the dental tool and for transporting the dental tool from the positioner to the grinding surface while maintaining the top face substantially perpendicular to the axis of rotation of the grinding surface.

2. The dental tool sharpener of claim 1, wherein the positioner further comprises a top surface and an alignment surface attached to the top surface, and wherein the top surface and the alignment surface are substantially perpendicular to the axis of rotation of the grinding surface.

3. The dental tool sharpener of claim 2, wherein the positioner further comprises a dial for vertically adjusting the position of the alignment surface with respect to the top surface.

4. The dental tool sharpener of claim 2, wherein the top surface further comprises a groove running across at least a portion of the top surface.

5. The dental tool sharpener of claim 1, wherein the grinding surface is conically-shaped.

6. The dental tool sharpener of claim 1, wherein a top face and a side face of the blade form a contact angle, and wherein the grinding surface further comprises a contact surface set at an angle relative to the base, the contact surface and the base forming a contact angle of the grinding surface, and wherein the contact angle of the blade and the contact angle of the grinding surface are complementary.

7. The dental tool sharpener of claim 6, wherein the contact angle of the blade is approximately 72 through 76 degrees inclusive.

8. The dental tool sharpener of claim 1, wherein the gripper further comprises an articulated arm for transporting the dental tool between the positioner and the grinding surface.

9. The dental tool sharpener of claim 8, wherein the gripper further comprises a pair of jaws located at an end of the articulated arm for grasping the dental tool.

10. The dental tool sharpener of claim 9, wherein the jaws grasp the shank of the blade of the dental tool.

11. The dental tool sharpener of claim 10, wherein the jaws further comprise a recess, and wherein the shank rests within the recess.

12. A dental tool sharpener, comprising:
    a base;
    a grinding surface rotatably attached to the base about an axis fixed at a predetermined angle relative to a plane parallel to the base, the grinding surface including a contact surface for contacting a blade of a dental tool;
    a gripper attached to the base for grasping the dental tool; and
    a positioner attached to the base for aligning a top face of the blade of the dental tool such that a contact angle of the blade and a contact angle of the contact surface are complementary, wherein the contact angle of the blade is defined by a top face and a side face of the blade and wherein the contact angle of the contact surface is defined by the contact surface and a plane parallel to the top face of the blade as aligned by the positioner.

13. The dental tool sharpener of claim 12, wherein the contact surface of the grinding surface is substantially perpendicular to the axis of rotation.

14. The dental tool sharpener of claim 12, wherein the contact surface of the grinding surface is substantially parallel to the axis of rotation.

15. The dental tool sharpener of claim 12, wherein the axis of rotation is substantially perpendicular to the base.

16. The dental tool sharpener of claim 12, wherein the positioner further comprises a top surface and an alignment surface for aligning the top face of the dental tool.

17. The dental tool sharpener of claim 16, wherein the positioner further comprises a dial for vertically adjusting the position of the alignment surface with respect to the top surface.

18. The dental tool sharpener of claim 16, wherein the top surface further comprises a groove running across at least a portion of the top surface.

19. The dental tool sharpener of claim 12, wherein the gripper further comprises an articulated arm for transporting the dental tool between the positioner and the grinding surface.

20. The dental tool sharpener of claim 12, wherein the gripper further comprises a pair of jaws located at an end of the articulated arm for grasping the dental tool.

21. The dental tool sharpener of claim 20, wherein the jaws grasp the shank of the blade of the dental tool.

22. The dental tool sharpener of claim 21, wherein the jaws further comprise a recess, and wherein the shank rests within the recess.

23. The dental tool sharpener of claim 12, wherein the contact angle of the blade is approximately 72 through 76 degrees inclusive.

24. A method for sharpening a blade of a dental tool with a dental tool sharpener, the dental tool sharpener having a base and a positioner, a gripper and a grinding surface each attached to the base, the method comprising:
   aligning a top face of the blade in the positioner such that the top face is set at a fixed angle relative to the grinding surface, wherein a contact angle of the blade is complementary to a contact angle of the grinding surface, and wherein the contact angle of the blade is defined by a top face and a side face of the blade and wherein the contact angle of the contact surface is defined by the contact surface and a plane parallel to the top face of the blade as aligned by the positioner;
   grasping a shank of the blade with the gripper;
   moving the dental tool with the gripper from the positioner to the grinding surface;
   contacting a first side face of the blade with a contact surface of the grinding surface; and
   passing the first side face over the contact surface.

25. The method of claim 24 further comprising:
   contacting a second side face of the blade with a contact surface of the grinding surface; and
   passing the second side face over the contact surface.

26. The method of claim 24, wherein aligning a top face of the blade in the positioner further comprises:
   placing a bottom edge of the blade upon a groove in a top surface of the positioner, wherein the top surface is oriented at the fixed angle relative to the contact angle of the grinding surface; and
   lowering an alignment surface attached to the top surface towards the top surface until the blade is secured between the top surface and the alignment surface, wherein the alignment surface is substantially parallel to the top surface.

27. The method of claim 24, wherein grasping a shank of the blade further comprises:
   grasping the shank of the blade with a pair of jaws;
   positioning the shank within a recess in the jaws;
   closing the jaws to secure the shank within the recess; and
   lowering the top surface away from the bar.

* * * * *